United States Patent [19]

Li

[11] Patent Number: 4,614,588

[45] Date of Patent: Sep. 30, 1986

[54] METHOD FOR SULFIDE TOXICITY REDUCTION

[75] Inventor: Alan Y. Li, Stamford, Conn.

[73] Assignee: Dorr-Oliver Incorporated, Stamford, Conn.

[21] Appl. No.: 768,391

[22] Filed: Aug. 22, 1985

[51] Int. Cl.[4] .............................................. C02F 3/28
[52] U.S. Cl. ................................... 210/603; 210/611; 210/614
[58] Field of Search .............. 210/603, 611, 609, 612, 210/613, 614, 615–617, 631, 916

[56] References Cited

U.S. PATENT DOCUMENTS

| | | | |
|---|---|---|---|
| 3,105,014 | 9/1963 | Harrison | 210/603 X |
| 4,067,801 | 1/1978 | Ishida et al. | 210/603 |
| 4,200,523 | 4/1980 | Balmat | 210/611 |
| 4,351,729 | 9/1982 | Witt | 210/603 |
| 4,384,956 | 5/1983 | Mulder | 210/603 |
| 4,396,402 | 8/1983 | Ghosh . | |

*Primary Examiner*—Tom Wyse
*Attorney, Agent, or Firm*—Burtsell J. Kearns; Gary R. Plotecher; Paul D. Greeley

[57] ABSTRACT

A method and system for reducing the sulfur concentration of wastewater which is to be disposed of through anaerobic treatment. Wastewater high in sulfur content is fed to a reactor having a pH level less than 6, such that the sulfate and/or sulfite compounds in the wastewater are converted by sulfate reducing bacteria into sulfide gas, thereafter exhausting the sulfide gas from the reactor. It is preferred that two anaerobic reactors be connected in series, such that the first reactor contains sulfate reduce bacteria and/or acid-forming bacteria, and the second reactor contains methane-forming bacteria and/or acid-forming bacteria.

4 Claims, 3 Drawing Figures

METHOD FOR SULFIDE TOXICITY REDUCTION

BACKGROUND OF INVENTION

The present invention provides a novel method and system for reducing the sulfur (sulfates or sulfites) content of a wastewater stream to be treated anaerobically. The reduction of sulfur content in wastewater according to the present invention provides for feeding of wastewater high in sulfur content to a reactor and maintaining the reactor at a pH level less than 6, wherein the sulfate and/or sulfite compounds in the wastewater are converted into sulfide gas and exhausted from the reactor.

Two-phase anaerobic processes are well known as demonstrated in U.S. Pat. Nos. 4,067,801, 4,318,993 and 4,022,665. The anaerobic process is the use of a biological process for the stabilization of organic material by conversion to methane gas in the absence of oxygen. The process normally consist of two groups of bacteria, acid-forming bacteria which convert organics to volatile acids and finally to acetic acids and $H_2$, and a second group of methane-forming bacteria which convert acetic acids, $H_2$ and $CO_2$ to methane gas. Although both acid-forming bacteria and methane-forming bacteria may operate concurrently in a single reactor it is preferable, as described in the aforementioned patents, to have separate reactors for acid fermentation and methane fermentation.

This two-phase anaerobic process for treating wastewater is satisfactory in most instances. However, in instances where the wastewater is high in sulfate ($SO_4^=$) and sulfite ($SO_3^=$) content, such as wastewater from pulp and paper processing, the sulfates and sulfites are reduced to sulfides under conditions of an anaerobic reactor. Sulfides, such as $H_2S$ and $HS^-$, are known to be toxic to methane-forming bacteria at a level as low as 150 mg/liter, and as such many sulfate and/or sulfite containing wastewaters cannot be treated or disposed of anaerobically.

If sulfates and sulfites are present in a wastewater at a concentration above 150 mg/liter then they may be toxic to methane-forming bacteria, thus preventing or slowing the conversion of acetic acid, $H_2$ and $CO_2$ to methane gas. This effectively prevents the use of anaerobic systems in the treatment of sulfur containing wastewaters. The addition of metal salts, such as ferrous or ferric chloride, to the reactor to precipitate out of the metal sulfides has been used to reduce the sulfide concentration to allow anaerobic treatment of wastewaters high in sulfur content as described in U.S. Pat. No. 4,318,993. However, the effect of ferrous ions in the anaerobic process, and the cost of chemicals required, have reduced the effectiveness of the anaerobic process for handling these types of wastewaters.

Thus, the present inventor has discovered a method and system for sulfide toxicity reduction in the anaerobic treatment of wastewater high in sulfur content which is both economical and satisfactory in anaerobically treating such wastewaters. The present invention overcomes the problems and expense involved in reducing the sulfide contents in wastewater by means of addition of metal salts or chemicals such as ferric or ferrous chloride to precipitate out metal sulfites and removal of sulfide precipitates from the reactor. Additional advantages of the present invention shall become apparent as described below.

SUMMARY OF THE INVENTION

It is the primary object of the present invention to provide a method and system for sulfide toxicity reduction in wastewater high in sulfur content. In particular, the object of the present invention is to reduce the sulfur concentration of a wastewater, to be disposed of through anaerobic processing, by feeding the wastewater to a reactor, maintaining the reactor at a pH level less than 6 and converting sulfate and/or sulfite compounds in said wastewater into sulfide gas thereafter exhausting the sulfide gas from the reactor. It is also an object of the present invention to provide a sulfate reducing bacteria as the means for converting the sulfate and sulfite compound to sulfide gas.

The sulfate reducing bacteria may be one selected from the group consisting of Desulfovibrio, Desulfotomaculum, Desulfobactera and Desulfobulbus.

Preferably, it is an object of this invention to include two anaerobic reactors in series with sulfate reducing bacteria in a first reactor for converting the sulfates and sulfites in the wastewater into sulfide gas, and the acid-forming and the methane-forming bacteria in a second reactor for converting the organics via organic acids to methane gas. It is also an object of the present invention that the acid-forming bacteria used for converting organics to organic acids are contained in either or both of the reactors. It is also desirable according to the present invention that the first reactor have a pH level less than 6 and that the second reactor have a pH level of approximately 7.

The present invention may also include additional features which are described below.

DESCRIPTION OF THE PREFERRED EMBODIMENT

Figure 1:
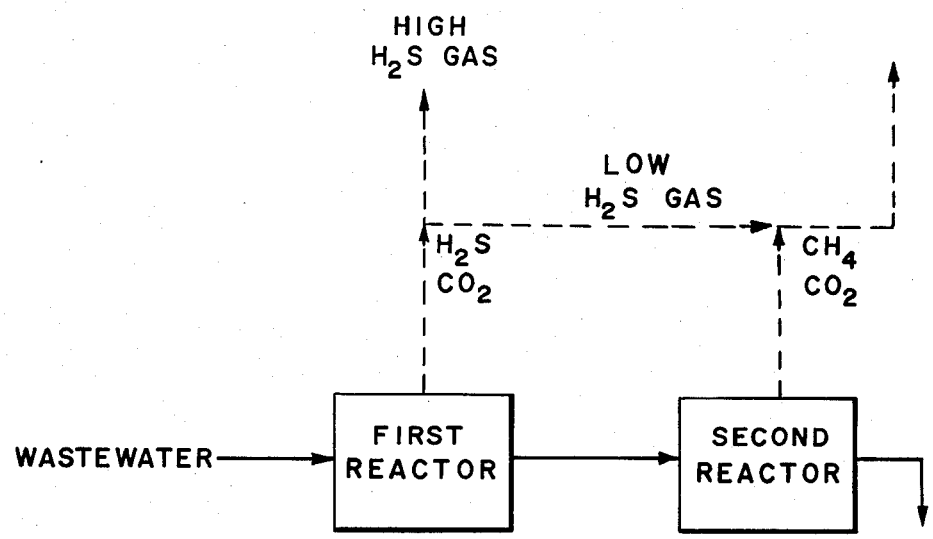
FIG. 1 is a flow sheet describing treatment of wastewater according to the present invention.

The method and system according to the present invention provides a novel means for reducing the sulfur content of a wastewater to be treated under anaerobic conditions. This method and system is preferably used when the sulfate or sulfite concentration of a wastewaster is greater than 150 mg/l. That is, when the sulfate or the sulfite content exceeds the aforementioned concentration level it has been found that the sulfides converted from the sulfate and/or sulfite are toxic to methane-forming bacteria and substantially reduce the rate of conversion of organic material to methane.

The present invention preferably includes the use of two anaerobic reactors, such reactors can be fluidized bed reactors, in series with the sulfate reducing bacteria (SRB) in the first reactor for conversion of the sulfates and/or sulfites in the wastewater to sulfide gas, and the acid and methane-forming bacteria mainly in the second reactor for conversion of organics via organic acids to methane gas. Most of the sulfides produced in the first reactor will be in gas form ($H_2S$) and can be readily exhausted from the first reactor so that the wastewater will not be toxic to the methane-forming bacteria in the second reactor. To achieve this, the present inventor has discovered that certain environmental conditions in the first reactor must occur, i.e. pH level should be below 6, such that more than 90% of sulfides will be $H_2S$ (gas), instead of $HS^-$ (soluble). Maintaining the pH level in the first reactor below 6 is also conducive to acid-forming bacteria which convert organics to organic acid.

The second reactor will be controlled as close to a pH level of 7 as possible for promoting growth of methane-forming bacteria. If the pH level of the first reactor exceeds 6.0 then the environment of the reactor would allow sulfide to remain in the wastewater as it moves to the second reactor which may be toxic to the methane-forming bacteria. SRB can be found in all natural anaerobic environments where sulfate is available such as sulfate-containing wastewater. Examples of SRB are genera such as Desulfovibrio, Desulfotomaculum, Desulfobactera, and Desulfobulbus. The genus Desulfovibrio, particularly Desulfovibrio Desulfurcans, is the most widely found in wastewaters. These bacteria are mesophilic, strict anaerobic curved rods having a single polar flagellum.

The environmental conditions that favor the growth of SRB's are also favorable to the acid-forming bacteria. Thus, it will be expected that the acid-forming bacteria will also proliferate in the first reactor unless the sulfide concentration is to high and become toxic to the acid formers. The carbon requirements for the SRB's can be derived from the volatile acids produced by the acid-forming bacteria although other carbon sources such as lactic, malic, and pyruvic acids are preferred by the SRB.

The utilization of acetic acids during sulfate reduction is illustrated in the following biochemically stoichiometric equation:

The gas generated from the first reactor consists essentially of $H_2S$ and $CO_2$, the by products of sulfate reduction and acid formation. $H_2$ may also be present if $CH_4$ cannot be found in the gas or visa versa, since $H_2$ and $CO_2$ will be reduced immediately to $CH_4$ in the presence of methanogens. The first reactor gas can be combined with the gas generated from the second stage reactor, which is expected to contain high $CH_4$ content, for further use if the quantity of $H_2S$ is low. However, if the $H_2S$ gas exhausted from the first reactor is present in large quantities, downstream process of the $H_2S$ gas to recover sulfur either in the form of element S or sulfuric acid can be achieved chemically or biologically. Commercial $H_2S$ oxidation processes are available.

This invention is not limited to any specific anaerobic process. The first and second reactors, shown in FIG. 1, can be any of the following, such as anaerobic contact, upflow or downflow anaerobic filters, upflow anaerobic sludge blankets, anaerobic fluidized beds or a combination of the aforementioned. However, the efficiency of the process can be improved if high rate processes such as anaerobic fluidized bed, shown in FIG. 2, are used.

Figure 2:
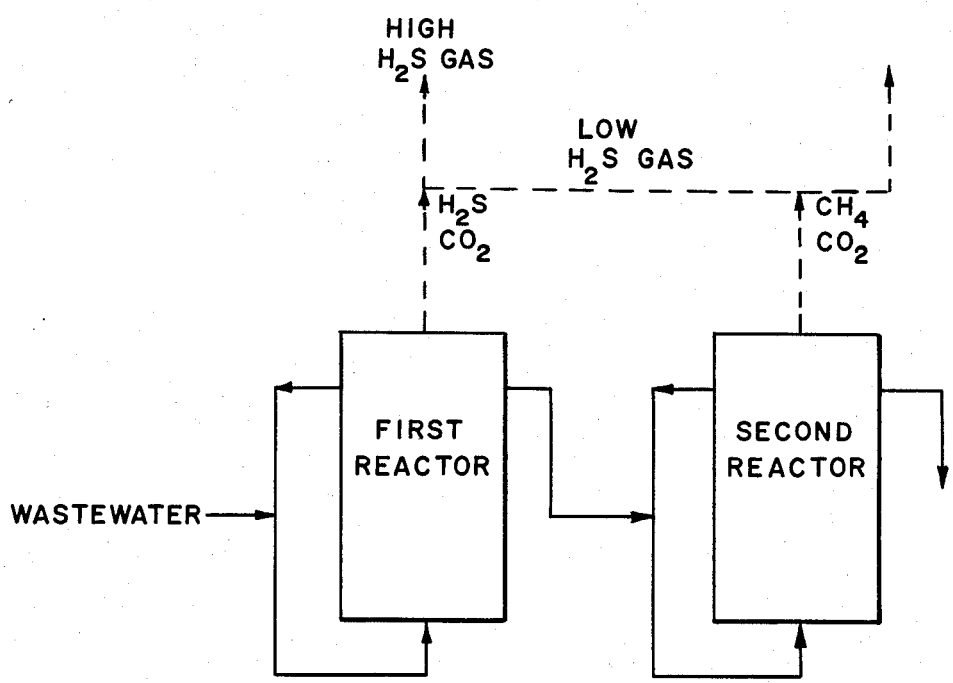
FIG. 2 is a flow sheet according to the present invention describing the use of fluidized bed reactors as the first and second reactors.

FIG. 1 describes a two-stage anaerobic reactor process for sulfide toxicity reduction according to the present invention. Wastewater high in sulfur content (sulfates and/or sulfites) is introduced into a first reactor for desulfurization.

In the first reactor of FIG. 1 the following reaction occur:

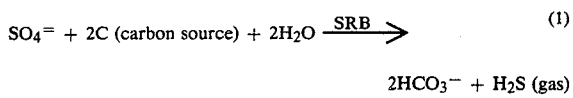

$$2HCO_3^- + H_2S \text{ (gas)}$$

The method and system described in FIG. 1 above for sulfide toxicity reduction is particularly suitable for the treatment of pulp and paper wastewater which contains sulfate and/or sulfite compounds much higher then 150 mg/liter. By controlling the pH of the first reactor below 6.0, not only sulfate or sulfite reduction will occur but the product sulfides will be in gas form ($H_2S$ instead of $HS^-$), and thus the gaseous sulfide can be removed from the reactor easily together with acidification products such as $CO_2$ and $H_2$.

Desulfurized wastewater is thereafter fed from the first reactor to a second reactor as shown in FIG. 1, where organics in the desulfurized wastewater are converted by methane-forming bacteria via organic acids to methane. Thereafter, methane gas and $CO_2$ are exhausted from the second reactor for further purification of the methane gas generated during the anaerobic process. The effluent liquid is discharged from the second reactor for further downstream treatment or immediate disposal into the environment. The gases generated from the first and second reactors can be treated as follows: high $H_2S$ gas can be sent to a sulfur recovery process downstream and low $H_2S$ gas can be combined with the gas generated from the second stage reactor for further use.

FIG. 2 describes the use of fluidized bed reactors as the first and second reactors in a method and system for sulfide toxicity reduction according to the present invention. FIG. 2 also provides for the recycling of waste treatment and effluent in the first and second reactors.

Figure 3:
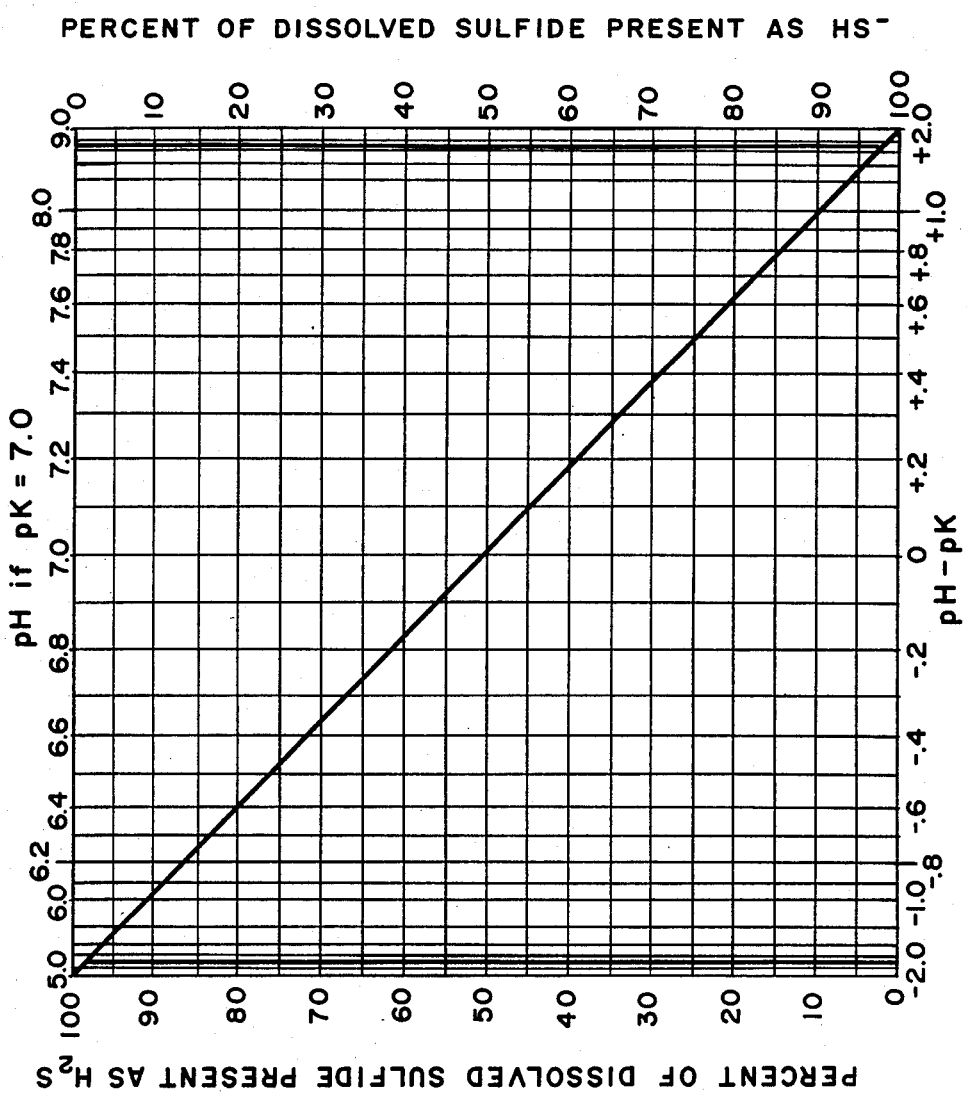
FIG. 3 is a graph plotting pH against the percent of dissolved sulfide present in the reactors.

FIG. 3 demonstrates the percent of dissolved sulfide present as $H_2S$ versus the percent of dissolved sulfide present as $HS^-$ as a function of the pH level in the reactor. As the pH level approaches 5.0 approximately 100% of the sulfide generated in the first reactor are in the form of $H_2S$ (gas) and can be readily exhausted from the system with minimal formation of $HS^-$. However, as the pH level becomes higher than 6.0 the percent of dissolved sulfide present as $H_2S$ and $HS^-$ begins to rapidly change. It is preferable that all of the sulfide present in the wastewater be converted to $H_2S$ gas for easy removal from the first reactor since sulfide present as $HS^-$ will be transported along with the wastewater to the second reactor which would be toxic to the methane-forming bacteria.

This application is not limited to the specific configurations shown herein and it is envisioned that numerous types of reactors and bacteria may be used to accomplish the same task within the parameters and environmental conditions setforth herein.

What is claimed is:

1. A method of sulfide toxicity reduction in two-phase anaerobic treatment of organic wastewater high in sulfur content comprising:
  feeding said organic wastewater to a first reactor;
  maintaining said first reactor at a pH in the range between 5-6;

converting sulfate and/or sulfite compounds in said organic wastewater into sulfide gas by means of a sulfate reducing bacteria, thereafter exhausting said sulfide gas from said first reactor; and feeding the desulfurized wastewater to a second reactor having a pH around 7 for converting the organics in said desulfurized wastewater first to organic acids then to methane gas and recovery of said gas; whereby at least 90% of the sulfur contained in said organic wastewater is exhausted from said first reactor such that said second reactor has a much reduced sulfur content in the wastewater received via said first reactor.

2. The method for sulfide toxicity reduction according to claim 1, wherein said sulfate reducing bacteria is one selected from the group consisting of Desulfovibrio, Desulfotomaculum, Desulfobactera and Desulfobulbus.

3. The method for sulfide toxicity reduction according to claim 1, wherein said first and second reactors are selected from the group consisting of anaerobic contact, up flow anaerobic filters, downflow anaerobic filters, upflow anaerobic sludge blankets, anaerobic fluidized beds and any combination of the aforementioned reactors.

4. The method for sulfide toxicity reduction according to claim 1, wherein said means for converting organic acids is an acid-forming bacteria, and means for converting said organic acids to methane gas is a methane-forming bacteria.

* * * * *